United States Patent [19]

Taniguchi

[11] Patent Number: 4,759,362
[45] Date of Patent: Jul. 26, 1988

[54] CAUTERIZING HEMOSTATIC EQUIPMENT

[75] Inventor: Akira Taniguchi, Hachioji, Japan

[73] Assignee: Olympus Optical Co., Ltd., Tokyo, Japan

[21] Appl. No.: 42,582

[22] Filed: Apr. 21, 1987

Related U.S. Application Data

[63] Continuation of Ser. No. 802,297, Nov. 27, 1985, abandoned.

[30] Foreign Application Priority Data

Nov. 28, 1984 [JP] Japan ................... 59-251234

[51] Int. Cl.⁴ ............................................. A61B 17/36
[52] U.S. Cl. ................................................ 128/303.1
[58] Field of Search ........... 128/303.1, 303.12, 303.17, 128/362, 399, 401, 423 R

[56] References Cited

U.S. PATENT DOCUMENTS

| | | | |
|---|---|---|---|
| 4,074,719 | 2/1978 | Semm | 128/303.1 |
| 4,231,371 | 11/1980 | Lipp | 128/303.1 |
| 4,266,556 | 5/1981 | Barlow et al. | 128/303.1 |
| 4,364,390 | 12/1982 | Shaw | 128/303.1 |
| 4,449,528 | 8/1984 | Auth et al. | 128/303.1 |
| 4,532,414 | 7/1985 | Shah et al. | 128/399 |
| 4,574,801 | 3/1986 | Manes | 128/303.14 |
| 4,580,557 | 4/1986 | Hertzmann | 128/303.1 |
| 4,582,057 | 4/1986 | Auth et al. | 128/303.1 |
| 4,691,703 | 9/1987 | Auth et al. | 128/303.1 |

FOREIGN PATENT DOCUMENTS

58-69556 6/1973 Japan.

OTHER PUBLICATIONS

"Transducers for Biomedical Measurements", by R. Cobbold; John Wiley & Sons, New York; 1974, pp. 80–81.

*Primary Examiner*—Lee S. Cohen
*Assistant Examiner*—David Shay
*Attorney, Agent, or Firm*—Armstrong, Nikaido, Marmelstein & Kubovcik

[57] ABSTRACT

A device to stop bleeding of a part by supplying a heating current to and heating a heating element which is contained in the end part of a probe and whose voltage drop at its ends shows temperature dependency and by applying the end part to the bleeding part. The device includes a resistance installed in series with the heating element, compares the voltage of the resistance with a reference voltage, and controls the heating current value using the comparison output which depends on the temperature increase of the heating element, thus keeping the heating temperature at a temperature suitable for stanching.

4 Claims, 2 Drawing Sheets

CAUTERIZING HEMOSTATIC EQUIPMENT

This application is a continuation of application Ser. No. 802,297 filed Nov. 27, 1985, now abandoned.

FIELD OF THE INVENTION AND RELATED ART STATEMENT

This invention relates to a cauterizing hemostatic equipment which can control the heating temperature of the heating element at the end of the probe.

Recently we see a wide use of the endoscope which can diagnose or treat a deep part in the body cavity by inserting a narrow and long inserting part, making it unnecessary to incise the body wall.

The said endoscope is usually provided with a hollow channel through which a treating tool can be passed, in addition to an observing means, and can make various treatment with the treating tool passed through the channel.

By the way, as a means to stop bleeding after a tumor in the body cavity is cut and eliminated, there is a laser coagulating device to irradiate the laser beam and coagulate the blood, but it is high in cost, requires skill, and involves danger.

For this reason there was developed a device which uses a heating probe which can be inserted through the channel and coagulates a bleeding part by energizing the heating coil provided at the end of the heating probe.

This device had a disadvantage that it destroyed other tissue than the target part because it had low responsiveness in raising and lowering the temperature, thereby increasing the quantity of heat to be conducted to the peripheral tissue during the time to reach the coagulating temperature or the cooling time after coagulating.

For this reason, as disclosed in the U.S. Pat. No. 4,449,528 (Japanese Patent Journal No. 58-69556), there is proposed a cauterizing hemostatic device to use a heating element which has good heating and cooling responsiveness for the cauterizing probe (heater probe) which can be inserted through the channel.

Since the prior art device uses a Zener diode or electron avalanche diode with small heat capacity (i.e. small volume and mass) as the heating element, it has good thermal responsiveness when the power supply to the heating element is controlled ON or OFF, has almost no such disadvantage as to destroy the peripheral tissue, and can stanch only a desired part.

In the prior art, however, the calorific value produced by the heating element is constant, and therefore, the heating temperature is changed because the heat dissipation differs depending on the state of the tissue onto which the end part containing the heating element is pressed, thus making it impossible to perform the styptic treatment at a proper temperature.

OBJECT AND SUMMARY OF THE INVENTION

The object of this invention is to provide a cauterizing hemostatic device which can provide an effective styptic treatment by maintaining a proper heating temperature even when the heat dissipation at the probe end is changed.

Another object of this invention is to provide a cauterizing hemostatic device which can perform the styptic treatment in a highly safe manner.

This invention is a device which has a heating element with small heat capacity and good thermal responsiveness housed in the end part of a narrow and long probe and performs the styptic treatment by supplying the heating current to the heating element, and detects the voltage at both ends of a resistance installed in series with the heating element, compares the voltage with a reference voltage, and maintains a proper stanching temperature of the heating element using the comparison output.

BRIEF DESCRIPTION OF THE DRAWINGS

FIG. 1 is a circuit diagram to show the main parts of the probe driving circuit of the first embodiment, FIG. 2 a perspective side view to show the external appearance of the first embodiment, and FIG. 3 a characteristic diagram to show the current characteristics in the operating state of the first embodiment.

DETAILED DESCRIPTION OF PREFERRED EMBODIMENT

Figure 1:
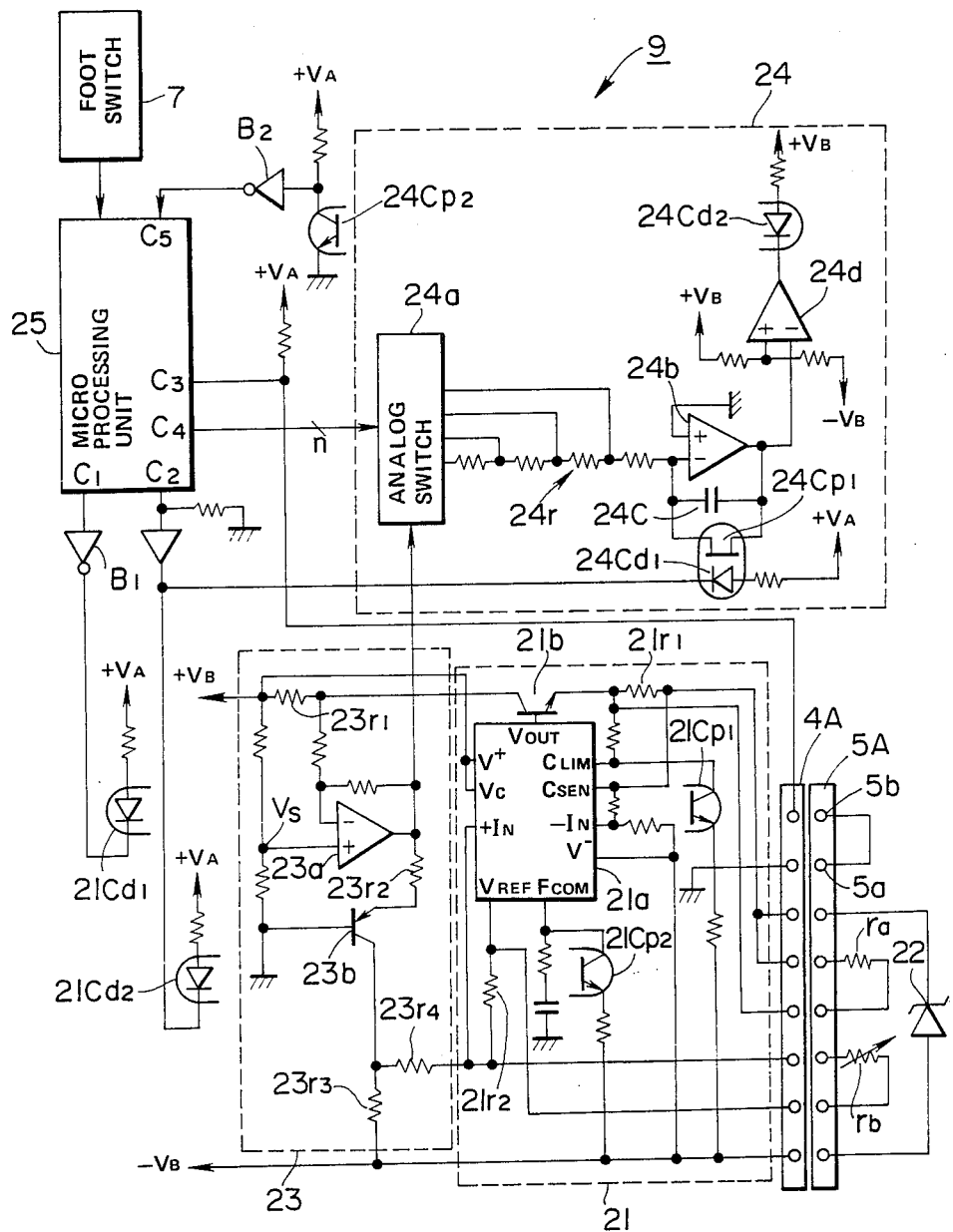
FIGS. 1 to 3 relate to the first embodiment of this invention.
Figure 2:
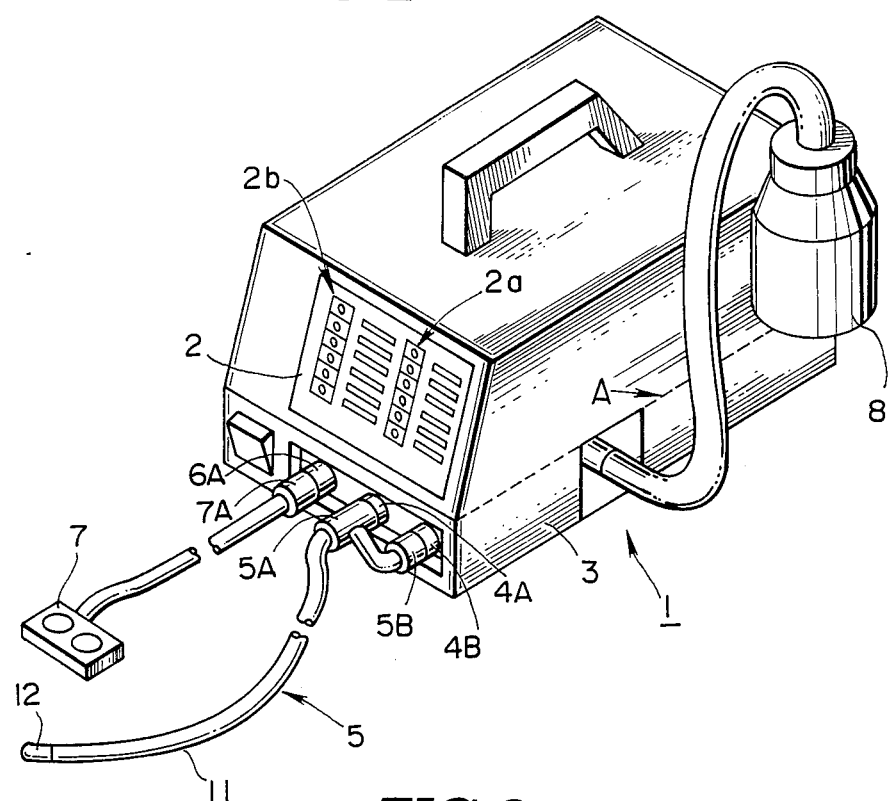

As shown in FIG. 2, the cauterizing hemostatic device 1 of the first embodiment consists of a power box 3 provided with an operating panel 2 on the front slant face, narrow and long heater probe 5 whose connectors 5A and 5B can be detachably fixed to the connector receptacles 4A and 4B at the front lower part of the power box 3, foot switch 7 whose connector 7A can be detachably fixed to the connector receptacle 6A provided at the front lower part of the power box 3, water supply tank 8 provided at a side, and probe driving circuit 9 provided in the power box 3 and shown in FIG. 1.

For the heater probe 5 a coaxial cable is passed through a narrow and flexible probe part 11 which can be inserted through a hollow channel of an endoscope (not illustrated) to energize a heating element with small heat capacity contained in the end part 12 of the probe part 11, and also in the probe part 11, a water supply passage is provided to supply washing water. With the electric connector 5A and water supply connector 5B of the heater probe 5 fixed to the connector receptacles 4A and 4B of the power box 3 and the connector 7A of the foot switch 7 fixed to the connector receptacle 6A of the power box 3, if the water supply switch of the foot switch 7 is pressed, the washing solution in the water supply tank 8 is supplied through the water supply passage and sprayed onto an affected part through the nozzle of the end part 12 of the heater probe or if the heating switch of the foot switch 7 is pressed, power is supplied through the coaxial cable to heat the heating element making it possible to perform the styptic treatment, etc.

The amount of the washing solution and sprayed amount of heat provided by the heating element can be set with the setting buttons 2a and 2b provided on the panel 2 in accordance with the condition of the affected part.

For the power box 3, safety is secured by providing an intermediate chassis, for example, at the position shown by a broken line A of the power box 3 in FIG. 2, thus separating the electric system, upper part, and water supply system, lower part, and the production process can be made easier by making each system separately and then assembling them into a finished product.

By the way, the main parts of the probe driving circuit 9 as an electric circuit to supply the cauterizing (heating) current to the heater probe 5 are shown in FIG. 1.

The probe driving circuit 9 consists of a constant-current circuit 21, Zener diode 22 with the electron avalanche characteristic whose Zener voltage shows temperature dependency, as a semiconductive heating element, to which the constant current is supplied by the constant-current circuit 21, heating temperature controlling circuit 23 which takes in the current supplied to the Zener diode 22 and controls the heating temperature at the Zener diode 22 through positive feedback, calorific value detecting circuit 24 to detect whether the preset gross calorific value is reached or not, and one-chip micro processing unit (hereinafter referred to MPU) 25 to control these circuits.

The constant-current circuit 21 uses the constant-voltage IC 212 (e.g. uA 723) to apply the voltage of the control output end $V_{OUT}$ of the contant-voltage IC 21a to the base and controls the collector/emitter current of the controlling transistor 21b, thus making it possible to control to a prescribed current value, e.g. 540 mA or 430 mA depending on the large diameter or small diameter of the heater probe 5. For example, when the large-diameter heater probe 5 is installed (in this case the resistance ra is connected to the connector 5A), it is possible through the resistance ra to make the current to the Zener diode 22 larger than the current for the small diameter. That is, due to the resistance ra, the combined resistance on the emitter side of the controlling tranistor 21b in the constant-current circuit 21 will become a small parallel resistance of resistance $21r_1$ and resistance ra, thus increasing the limited current value. (The voltage at both ends of the resistance $21r_1$ is sensed by the constant-voltage IC 21a).

Also, by adjusting that value by means of the variable resistance $r_b$ provided in the connector 5A, it is possible to set to a proper current value even if there is a dispersion in the Zener voltage Vz of the Zener diode 22. In addition, it is possible to set easily to a proper current value according to insert resistance in Zener diode in series at probe side.

The said constant-voltage IC 21a is provided with the current limiting terminal $C_{LIM}$ to which a photo transistor 21 $C_{P1}$ to form a photo coupler is connected, and when the light emission diode (LED) $21C_{d1}$ to make a pair with the photo transistor $21C_{p1}$ emits light, continuity (ON) occurs to release the output current limiting. The light emission diode $21C_{d1}$ to form the photo coupler has its anode connected via a resistance to the (positive) power supply end $V_A$ (+5 V) and its cathode connected to the terminal $C_1$ of the MPU 25 which functions as a control circuit, via the buffer $B_1$ of the open collector inverter, and when the output level of the terminal $C_1$ becomes high, the LED $21C_{d1}$ emits light.

The output current of the constant-current circuit 21 is cut off when the photo transistor $21C_{p2}$ connected to the frequency compensating terminal $F_{COM}$ is turned ON. The LED $21C_{d2}$ to make a pair with the photo transistor $21C_{p2}$ is controlled by the output level of the terminal $C_2$ of the MPU 25.

By the way, when the connector 5A is connected to the connector receptacle 4A, the MPU 25 can detect the connection because through the terminal 5a and 5b, the output of terminal $C_3$ changes from high level to low level. If the terminal $C_3$ output is at high level, therefore, the heating power is not output.

By the way, the collector of the controlling transistor 21b is connected to the heating power supply end $V_B$ (+15 V) via the resistance $23r_1$ (in the heating control circuit 23), and the potential of the voltage drop due to the resistance $23r_1$ is applied to the inverted input end of the operational amplifier 23a and the other input end is maintained at the reference potential Vs. The operational amplifier 23a amplifies the voltage between both input ends, e.g. 3.9 times, and the output is applied to the input end of the analog switch 24a of the calorific value detecting circuit 24 and also supplied to the negative power supply end $-V_B$ via the resistance $23r_2$, emitter/collector of transistor 23b and resistance $23r_3$.

The current running through the resistance $23r_2$, transistor 23b and resistance $23r_3$ changes the potential at the connecting point of the resistance $23r_3$ and the collector of the transistor 23b, and the potential then changes the voltage at the (non-inverted) control input end $I_N$ of the constant-voltage IC 21a via the resistance $23r_4$, and the voltage at the control input end $I_N$ changes the output level of the control output end $V_{OUT}$, thus controlling the heating current. In this case, the feedback loop is so set as to make positive feedback. For example, when the Zener diode 22 in series with the resistance $23r_1$ is used (when energizing and heating) and if the temperature increase of the Zener diode 22 is small as in the environment where the heat dissipation is easy, the temperature-dependent Zener voltage is also small in increasing and the current to run through the resistance $23r_1$ is larger than in the environment where the heat dissipation is difficult. Then, because the potential at the inverted input end decreases, the output level of the operational amplifier 23a rises, the potential of the collector of the transistor 23b also rises, the voltage at the control input end $I_N$ of the contant-voltage IC 21a also rises, the output level at the control output end $V_{OUT}$ also rises, and the heating current running through the controlling transistor 21b increases.

In the reverse case, i.e. if the current running through the resistance $23r_1$ is small as in the environment where the heat dissipation is difficult, the heating current decreases.

Thus the heating current to the Zener diode 22 is controlled so that the temperature-dependent Zener voltage will become constant, although the heating temperature of the end part 12 containing the Zener diode 22 tends to be changed due to the heat dissipation.

Thus the first embodiment is characterized in that it has a means to control and maintain the heating temperature of the said Zener diode 22 at a proper stanching temperature without being affected by the heat dissipation of the end part 12.

The said control input end $I_N$ is connected to the reference voltage end $V_{REF}$ via the resistance $21r_2$.

For the calorific value detecting circuit 24, the combination of the series resistances $24r$ at the output end (3 resistances are illustrated to be simple) to be shorted differs depending on the digital signals output from the terminals (group) $C_4$ of the MPU 25 making it possible to select the combined resistance. With the combined resistance and the capacity of the capacitor 24C connected between the inverted input end of the operational amplifier 24b and the output end the integral time constant of the integrating circuit can be selected.

Both ends of the capacitor 24C of the operational amplifier 24b to form the said integrating circuit are connected to the photo FET $24C_{p1}$, and when LED $24C_{d1}$ is emitting light, both ends of the capacitor are shorted, and the output of the operational amplifier 24b is maintained higher than the potential of the non-inverted input end of the next-stage operational amplifier 24d.

When the terminal $C_2$ of the said MPU 25 is made high level, the short-circuit of the capacitor $C_2$ is released and the integrating operation is started, and when the output of the operational amplifier 24b exceeds the reference level at the next-stage operational amplifier 24d, the output level of the operational amplifier 24d becomes high and the LED $24C_{d2}$ goes out. When the LED $24C_{d2}$ goes out, the pairing photo transistor $24C_{p2}$ is turned OFF and the terminal $C_5$ output level is made low via the buffer $B_2$. When the terminal $C_5$ output becomes low, for example the terminal $C_2$ voltage becomes low having the LED $21C_{d2}$ emit light and turning on the photo transistor $21C_{d2}$, and the current output from the constant-current circuit 21 to the load side is cut off.

When the foot switch 7 is turned on, the MPU 25 makes the output of terminal $C_1$ high having the LED $21C_{d1}$ emit light and turning on the pairing photo transistor $21C_{p1}$, releasing the current limiting function of the constant-current circuit 21. When the current limiting function is released and the positive feedback loop is operated by the heating control circuit 23, a high current runs to the Zener diode 22, and if the current runs, e.g. for 150 ms, the terminal $C_1$ output becomes low and is held to the current when the current limiting function operates. The current is integrated by the integrating circuit of the calorific value detecting circuit 24, and when it reaches the preset calorific value, the output level of the operational amplifier 24d becomes low, the LED $24C_{d2}$ emits light, terminal $C_5$ output becomes low, the terminal $C_2$ output is changed from high level to low level and the photo transistor $21C_{p2}$ is turned on, thus preventing the heating current from being applied.

The calorific value can be set using the setting button 2b on the panel 2.

For the Zener diode 22 as a heating element, its Zener voltage Vz shows temperature dependency (as the temperature increases, the Zener voltage Vz increases), and when it is heated due to the temperature dependency, the temperature increase changes depending on the heat dissipation at the end part 12. The temperature increase becomes the current change and the current change becomes the voltage drop at the resistance $23r_1$ and is detected by the operational amplifier 23a, and by means of the positive feedback loop including the operational amplifier 23a, the current amount is controlled. That is, when the temperature rises, the temperature of the end part 12 is prevented from rising by decreasing the current, and if the heat dissipation is high, the calorific value is increased so that a proper stanching temperature can be maintained.

The output current of the operational amplifier 23a of the heating control circuit 23 passes through the analog switch 24a and is integrated by the resistance selected from the resistance group 24r and the time constant of the capacitor 24C, and when it becomes a preselected current value, the output of the operational amplifier 24d becomes low and the terminal $C_5$ output becomes low. When the terminal $C_2$ output becomes low, the heating current is prevented from being applied.

The following will explain the operation of the first embodiment thus formed.

When the connector 5A of the heater probe 5 is connected, the terminal $C_3$ output becomes low and the microcomputer circuit 25 detects the connection. When the foot switch 7 is pressed, the terminal $C_1$ output becomes high and the photo transistor $21C_{p1}$ is turned on to release the output current limiting function, and then the terminal $C_2$ output is changed from low level to high level extinguishing the LED $24C_{d1}$ and turning off the photo FET $24C_{p1}$ and also extinguishing the LED $24C_{d2}$ and turning off the photo transistor $21C_{p2}$ so that the output current runs to the Zener diode 22. When the current runs through the resistance $23r_1$ of the heating control circuit 23, voltage drop occurs, and it is amplified by the operational amplifier 23a. The amplified output runs to the negative power supply $-V_B$ via the resistance $23r_2$, transistor 23b and resistance $23r_3$, and raises the potential at the control input $I_N$ of the constant-voltage IC 212, raises the output level at the control output end $V_{OUT}$, and increase the output current running through the controlling transistor 21b. The increase becomes an increase in the voltage drop at the resistance 24r and the above process is repeated, and by means of the positive feedback loop the output current is instantly increased to the current value (about 1.5A) (this value is shown as $I_{MAX}$ in FIG. 3) limited by the resistance $23r_1$, $21r_1$ and the Zener voltage Vz of the Zener diode 22.

This high current rapidly increases the temperature at the end part of the heater probe 5. This rapid heating is done for the time (150 ms) until the end part reaches the proper stanching temperature (surface temperature about 180° C.). The time is detected by the time counting means of the MPU 25 (timer IC can also be used), and after the elapse of that time, the terminal $C_1$ output becomes low, the LED 21C d1 extinguishes, the photo transistor $21C_{p1}$ of the constant-current circuit 21 is turned off, and the current limiting function works, and the maximum current is limited to 540 mA for the large-diameter heater probe 5 because of the resistance ra in the said heater probe or to 430 mA for the narrow-diameter probe because the resistance ra is not provided for this probe.

By the way, the Zener voltage Vz of the Zener diode 22 contained in the end part 12 of the heater probe 5 has, for example, the temperature coefficient of 0.4%/° C., and therefore, if the heat dissipation is small as when the end part 12 exists in the atmosphere, the heat dissipation at the end of the probe decreases and the temperature of the tip of the Zener diode 22 increases, and in such a state, the Zener voltage Vz increases (voltage increase rate becomes high) and the current to run to the Zener diode 22 decreases. Then the current decrease becomes a decrease in the voltage drop at the resistance $23r_1$ and by means of the aforementioned positive feedback loop, the current is further decreased. Then the current reaches a balanced current value $I_b$ at which the temperature increase due to the Zener diode 22 is offset by the current decrease caused through the positive feedback of the change in the Zener voltage Vz. Such current value is shown as symbol $I_{b2}$ in FIG. 3 (b).

Figure 3:
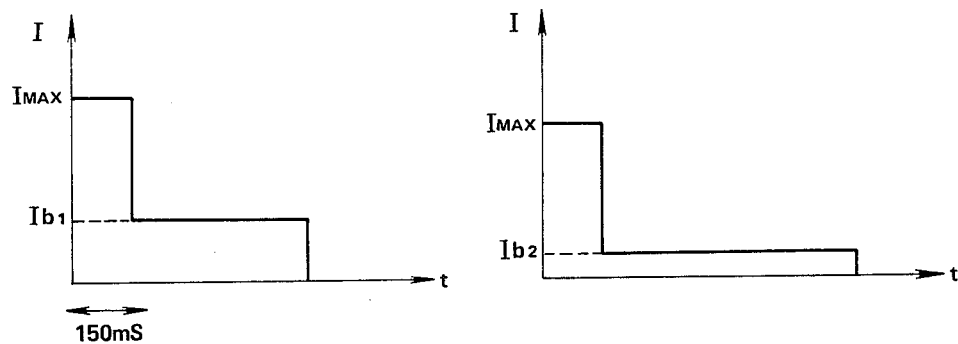

The said balanced current value $I_b$ depends on the heat dissipation of the probe tip, and for example, if the heat dissipation is good as at the affected part wet with water or blood, the temperature increase of the tip of the Zener diode 22 is small, and therefore, the Zener voltage Vz is also small in increasing and so the current decrease by means of the positive feedback loop for the change of the Zener voltage Vz in the heating control circuit 23 is also small. Therefore, if the heat dissipation is good, the heating current increases and the calorific value increases. Also the amount of heat dissipation is high, and therefore, a balance is kept at the balanced current value $I_b$ at which they are offset. FIG. 3 (a) shows the current running to the Zener diode 22 when the heat dissipation is larger than that of FIG. 3 (b).

Since the said positive feedback amount is set in accordance with the temperature coefficient of the Zener diode 22, the temperature of the probe tip is always kept at a temperature suitable for stanching in accordance with the heat dissipation. Therefore, such inconvenience that the heating current must be adjusted depending on the use environment can be eliminated.

It is also possible to set the reference potential Vs in the heating control circuit 23 by means of a variable resistance, etc. so that the stanching temperature can be fine-adjusted in accordance with the part to be stanched.

According to the aforementioned first embodiment, the end part 12 can be made small because the heating temperature of the heating element 22 contained in the end part 12 can be set to a proper stanching temperature despite the heat dissipation of the environment for the styptic treatment without providing a temperature sensor in the end part 12 of the heater probe 5 which is inserted through the channel of an endoscope.

Since the heating temperature can be controlled without changing the structure of the heater probe 11 itself, any heater probe using the heating element whose Zener voltage is temperature-dependent can be used almost without being affected by its structure.

The heating temperature controlling means is not limited to the aforementioned. If, for example, the Zener voltage Vz of the Zener diode 22 shows negative temperature dependency, negative current feedback can be adopted. It is also possible to contain a temperature sensor such as thermister and resistance bulb in the end part of the heater probe 5, compare the output of the sensor with the reference value using a comparator, and use the comparison output to keep the heating temperature of the heating element to a temperature suitable for stanching.

It is also possible to provide a temperature responsive fuse which is cut when the temperature rises to be abnormally high, in the end part where the heating element is contained and to supply the heating current to the heating element through the temperature responsive fuse. In such a case, even if the temperature at the end part becomes higher than the proper stanching temperature due to failure of the heating temperature control system, the temperature responsive fuse is cut, thus preventing the neighborhood of the part to be stanched from being hurt.

Although the MPU is used as a means to control the circuits in the aformentioned embodiment, it is also possible to operate each circuit directly.

The heating element is not limited to the Zener diode 22, and it is also possible to use any other semiconductor element which has the electron avalanche phenomenon.

It is clear that various embodiments over a wide range can be formed on the basis of this invention without deviating from the spirit and scope of this invention. This invention is not restricted by its particular embodiment except by the attached claims.

I claim:

1. A cauterizing hemostatic device comprising:
   a probe adapted to be inserted into a body cavity through a channel provided in an endoscope for insertion of a treating tool, said probe having at a front end (12) thereof a semiconductor heating element (22) of small heat capacity which has an electron avalanche characteristic, a voltage drop across said heating element at a constant current being dependent on the temperature thereof; and
   a current supply circuit connected to said heating element through a rear end connector of said probe, said current supply circuit including a constant current circuit means (21) for applying a constant heating current to said heating element at a set current level, and a heating control circuit means (23) connected to said constant current circuit means (21) for adjustably setting and controlling said level of constant current applied to said heating element (22);
   said current supply circuit constant current circuit means (21) including a first resistance means ($21r_1$, ra) connected in series with said heating element (22) and a transistor (21b) such that a voltage across said first resistance means varies in proportion to variations in said applied heating current, a reference voltage source ($23r_4$), and a voltage regulator (21a) to compare said first resistance means voltage with voltage of said reference voltage source and to control current through said first resistance means ($21r_1$, ra) so as to apply a constant current to said heating element; and
   said heating control circuit means (23) including a second resistance means ($23r_1$) connected in series with said transistor (21b), said first resistance means ($21r_1$, ra) and said heating element (22), and a comparator (23a) connected to both ends of said second resistance means ($23r_1$) to compare a voltage drop of said second resistance means with a voltage of said reference voltage source ($23r_4$), an output of said comparator (23a) being connected to said transistor (21b) to control current therethrough so that, by positive feedback of the heating current as measured by the voltage drop across said second resistance means ($23r_1$) the level of constant current from the constant current circuit means (21) will be set to make the sum of the voltages of the heating element (22) and the first resistance means ($21r_1$, ra) constant such that heating current will be increased with an increase of heat dissipation within said body cavity to maintain the temperature of said heating element (22) constant.

2. A cauterizing hemostatic device as recited in claim 1, wherein said current supply circuit reference voltage source includes means for adjusting said reference voltage.

3. A cauterizing hemostatic device as recited in claim 1, wherein said rear end connector of said probe includes a portion of said first resistance means (ra), which portion is connected in said constant current circuit means when connecting said probe, so as to preset said set level of heating current to a level appropriate for the characteristics of a connected probe.

4. A cauterizing hemostatic device as recited in claim 1 further comprising in said current supply circuit a calorific value detecting circuit means including an integrating circuit for integrating current applied to said heating element, means for setting a preset calorific value in said calorific value detecting circuit means, and control means for causing said heating control circuit means to apply a high heating current to said heating element until said preset calorific value is reached to bring said heating element to an operating temperature in a short period of time and to thereafter reduce said current to a lower level sufficient to maintain said operating temperature under control of said heating control circuit means.

* * * * *